US006159154A

United States Patent [19]

Takeuchi

[11] Patent Number: 6,159,154

[45] Date of Patent: Dec. 12, 2000

[54] IMAGING SYSTEM AND METHOD USING THERMALLY EXCITED MICROBALLOONS

[75] Inventor: Yasuhito Takeuchi, Tokyo, Japan

[73] Assignee: GE Yokogawa Medical Systems Limited, Tokyo, Japan

[21] Appl. No.: 09/227,120

[22] Filed: Jan. 9, 1999

[30] Foreign Application Priority Data

Mar. 5, 1998 [JP] Japan .................................. 10-053418

[51] Int. Cl.[7] .......................................... A61B 8/14

[52] U.S. Cl. .......................................... 600/458

[58] Field of Search .................................... 424/5.92, 450, 424/5; 600/458, 453, 440, 441, 437

[56] References Cited

U.S. PATENT DOCUMENTS 4,265,251 5/1981 Tichner .
5,149,319 9/1992 Unger .......................................... 600/437
5,315,998 5/1994 Tachibana et al. ........................ 600/437
5,833,615 11/1998 Wu et al. .................................. 600/458
5,848,968 12/1998 Takeuchi .................................. 600/458

FOREIGN PATENT DOCUMENTS 19725817 1/1998 Germany .

*Primary Examiner*—Marvin M. Lateef
*Assistant Examiner*—Ali M. Imam
*Attorney, Agent, or Firm*—Moonray Kojima

[57] ABSTRACT

In order to obtain an image of a microballoon contrast agent with sharpness, the invention comprises means for generating ultrasound 522 by thermally exciting the microballoon contrast agent infused in a subject to cause the microballoons to resonate, and means for producing an image 514 based on the generated ultrasound.

10 Claims, 6 Drawing Sheets

IMAGING SYSTEM AND METHOD USING THERMALLY EXCITED MICROBALLOONS

BACKGROUND OF THE INVENTION

The present invention relates to an ultrasonic imaging method and apparatus employing a microballoon contrast agent.

In ultrasonic imaging employing a contrast agent, the contrast agent comprises a large number of bubbles (microballoons) having a diameter on the order of a few micrometers in a liquid, and secondary harmonics echoes based on the non-linear echo source property of the microballoons is utilized to achieve the contrast imaging. The nonlinear echo source property arises from resonance of the microballoons with the frequency of the transmitted ultrasound.

Since the microballoons continue to resonate after the ultrasound pulse transmission is terminated, echo signals generated by the microballoons include, in addition to the main echo corresponding to the pulse width of the transmitted ultrasound, subsequent tailing. Each echo signal has a main echo return time representing the depth of the reflecting point, and hence the signal tailing causes image tailing in the image of the reflecting point. Accordingly, the generated contrast image has poor sharpness.

SUMMARY OF THE INVENTION

It is therefore an object of the present invention to provide an ultrasonic imaging method and apparatus which produce an image of a microballoon contrast agent with high sharpness (definition).

In accordance with a first aspect, the present invention provides an ultrasonic imaging method comprising the steps of: infusing a microballoon contrast agent into a subject; thermally exciting the microballoon contrast agent to cause the microballoons to resonate; and producing an image based on ultrasound generated by the resonance of the microballoons.

In accordance with a second aspect, the present invention provides an ultrasonic imaging apparatus comprising: means for generating ultrasound by thermally exciting a microballoon contrast agent infused into a subject to cause the microballoons to resonate; and means for producing an image based on the generated ultrasound.

In accordance with a third aspect, the present invention provides the ultrasonic imaging apparatus as described regarding the second aspect, wherein the means for generating ultrasound thermally excites the microballoon contrast agent utilizing electromagnetic waves, an electric field, a magnetic field or light to cause the microballoons to resonate, thereby generating ultrasound.

In accordance with a fourth aspect, the present invention provides the ultrasonic imaging apparatus as described regarding the second or third aspect, wherein the means for producing an image receives the generated ultrasound in a three-dimensional manner, and produces a three- or two-dimensional image based on the received signals.

In the first or second aspect of the invention, it is preferred that the microballoon contrast agent be thermally excited by the warming utilizing electromagnetic wave irradiation, because this effectively generates resonance of the microballoons.

Moreover, in any of the first—fourth aspects of the invention, it is preferred that a frequency translation be applied by subjecting the ultrasound generated by resonance of the microballoons to other ultrasound having a different frequency, because this enables the received ultrasound signals to be properly adjusted.

According to the present invention, ultrasound generated by the microballoons thermally excited to resonate are utilized to produce a spatial distribution image of ultrasound sources, i.e., the microballoons. Since the ultrasound generated by the microballoons are not echoes but spontaneous sound, there is no signal tailing.

The present invention thus implements an ultrasonic imaging method and apparatus which produces an image of a microballoon contrast agent with sharpness.

Further objects and advantages of the present invention will be apparent from the following description of the preferred embodiments of the invention as illustrated in the accompanying drawings.

DETAILED DESCRIPTION OF THE INVENTION

Preferred embodiments of the present invention will now be described in more detail with reference to the accompanying drawings.

Figure 1:
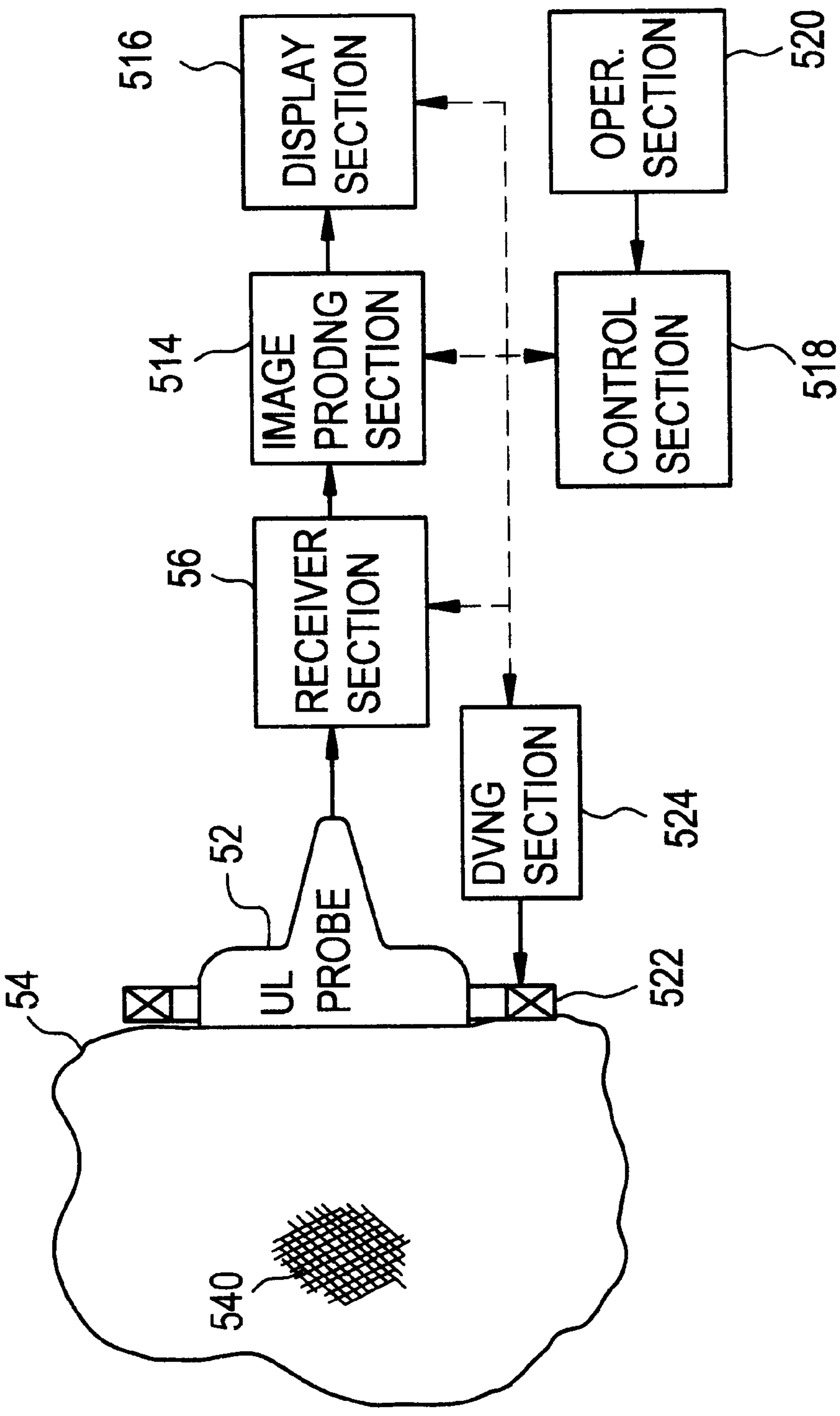
FIG. 1 is a block diagram of an apparatus in accordance with one embodiment of the present invention.

FIG. 1 shows a block diagram of an ultrasonic imaging apparatus. The apparatus is one embodiment of the present invention. The configuration thereof represents an embodiment of the apparatus of the invention, and the operation thereof represents an embodiment of the method of the invention.

As shown in FIG. 1, the apparatus includes an ultrasonic probe 52. The ultrasonic probe 52 is positioned to abut against a subject 54 and is used to receive ultrasound. The subject 54 has a microballoon contrast agent 540 infused therein beforehand. The ultrasonic probe 52 is provided with an electromagnetic wave irradiator 522 disposed nearby. The electromagnetic wave irradiator 522 consists of, for example, a solenoid coil and the like. The electromagnetic wave irradiator 522 is supplied with driving signals from a driving section 524 to irradiate the subject 54 with electromagnetic waves for warming.

The frequency of the electromagnetic waves is selected from values in the range between 10–2,450 MHz, for example. The electromagnetic wave irradiation is applied intermittently. The cycle of the intermittence is selected so that it is consistent with the resonance cycle, i.e., the reciprocal of the resonance frequency $f_s$ of the microballoons. The resonance frequency $f_s$ of the microballoons depends upon their diameter and is, for example, 1.6–2.5 MHz.

Figures 2A, 2B, 2C, 2D:
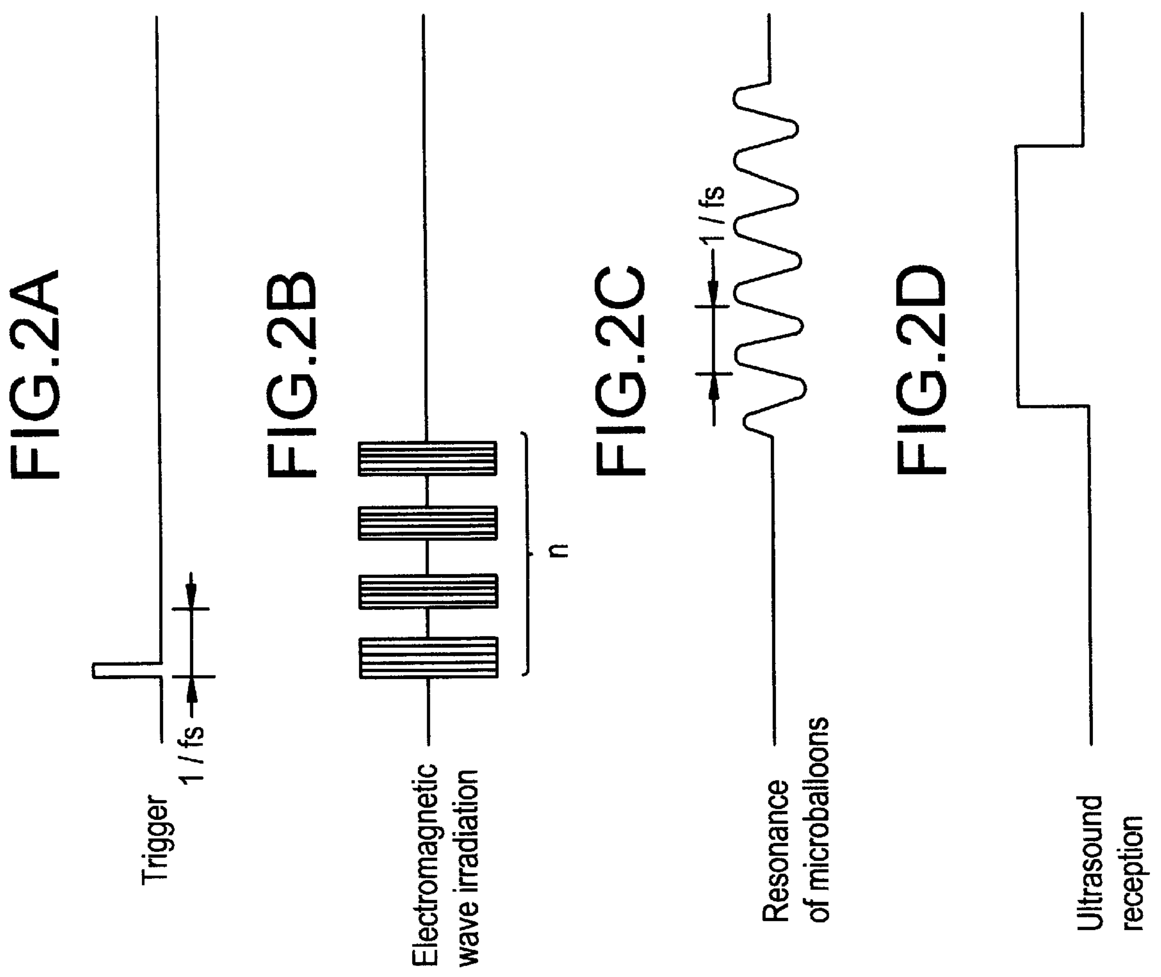
FIG. 2 illustrates the operation of the apparatus.

FIG. 2 illustrates an example of the electromagnetic wave irradiation process. Using a trigger signal (a) as a timing signal, the pulse-like electromagnetic wave irradiation is repeated 'n' times in a cycle $1/f_s$ as shown in (b). The number of the repetition, i.e., the number of bursts 'n', is 4–16, for example. The electromagnetic wave irradiation warms the interior of the subject 54 in a pulse-like manner.

The microballoons are thermally excited by the pulse-like warming and begin to expand and contract repeatedly. Since the cycle of the pulse-like warming is consistent with the resonance cycle of the microballoons, the microballoons come to resonate, thereby generating ultrasound. As shown in FIG. 2(*c*), the resonance continues after the electromagnetic wave irradiation is terminated, and hence the ultrasound also continues to be generated.

The ultrasound in this time period are received at a predetermined timing by the ultrasonic probe 52 as shown in FIG. 2(*d*). Since the microballoons which continue resonating are the only sources that continue generating the ultrasound even after the electromagnetic wave irradiation is terminated, the received ultrasound is generated exclusively from these microballoons. Such electromagnetic wave irradiation and ultrasound reception are repeated synchronously with trigger signals generated in a certain cycle.

The pulse-like warming may be successively applied without restriction on the number of bursts. This is preferable for simplifying control. If microballoons highly sensitive to resonance are employed, the number of thermally exciting pulses may be 1 (one-shot). This is preferable for reducing the electromagnetic wave irradiation.

Figure 3:
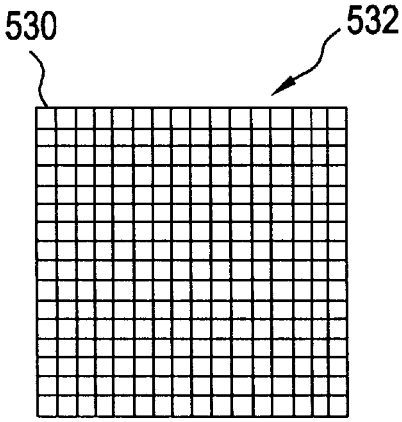
FIG. 3 is a schematic representation of an exemplary two-dimensional array of ultrasonic transducers in the apparatus.

Referring to FIG. 3, the ultrasonic probe 52 comprises a two-dimensional (2D) array 532 of ultrasonic transducers 530. The 2D array 532 consists of, for example, 128×128 ultrasonic transducers 530 forming a matrix. The ultrasonic transducers are composed of a piezoelectric material such as PZT (lead zirconate titanate) ceramic.

As shown in FIG. 1, the ultrasonic probe 52 is connected to a receiver section 56. The receiver section 56 receives the ultrasound signals picked up by the individual ultrasonic transducers 530 in the ultrasonic probe 52.

Figure 4:
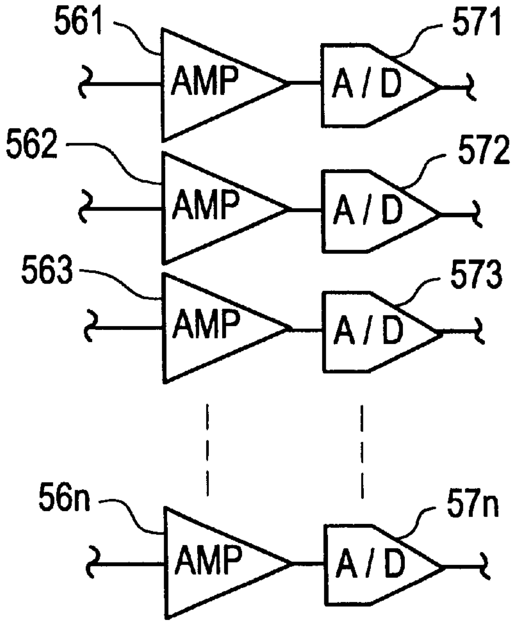
FIG. 4 is a block diagram of a receiver section of the apparatus.

As shown in FIG. 4, the receiver section 56 comprises a plurality of amplifiers 561–**56*n* and a plurality of AID (analog-to-digital) converters 571–57*n*. The amplifiers 561–56*n* and the A/D converters 571–57*n* are associated with the individual ultrasonic transducers 530 in the 2D array 532**.

The amplifiers 561–**56*n* amplify the ultrasonic signals received by the individual ultrasonic transducers 530. The AID converters 571–57*n* convert the respective analog output signals from the amplifiers 561–56*n*** into digital signals.

The individual ultrasonic signals received by the ultrasonic transducers 530 are thus converted into digital data with their RF (radio frequency) signal nature unchanged. These digital data form a holographic image of the ultrasonic signals received by the 2D array 532.

The receiver section 56 is connected to an image producing section 514. The digital data output from the receiver section 56 is supplied into the image producing section 514. The image producing section 514 produces an image representing distribution of the ultrasound sources within the subject 54 based on the digital data.

Figure 5:
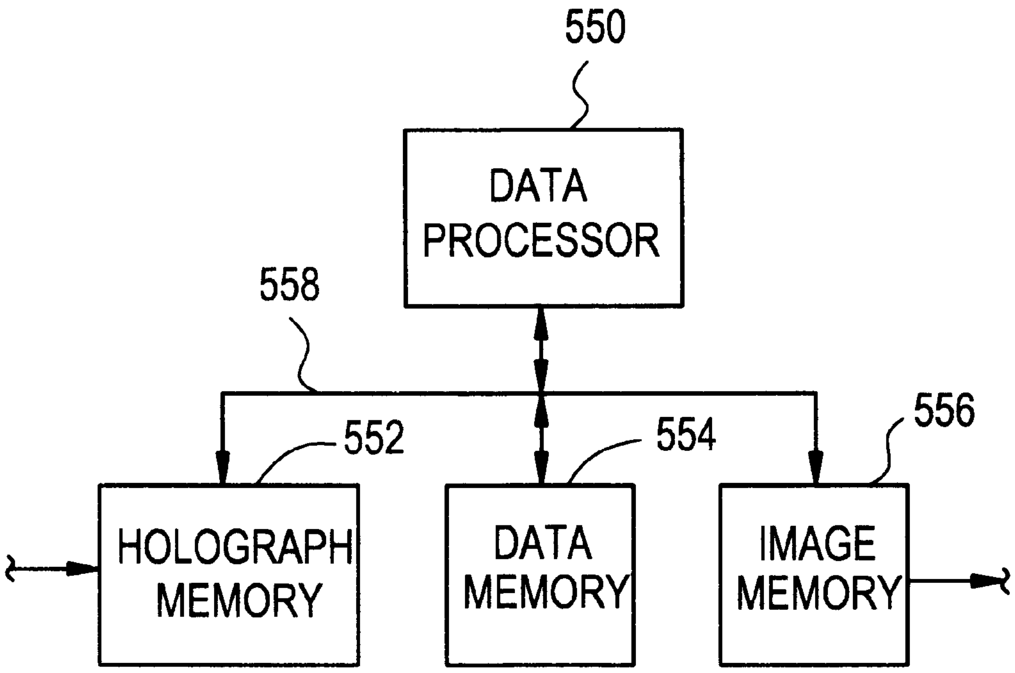
FIG. 5 is a block diagram of an image producing section of the apparatus.

Referring to FIG. 5, the image producing section 514 comprises a data processor 550, a holographic memory 552, a data memory 554 and an image memory 556. The data processor 550, the holographic memory 552, the data memory 554 and the image memory 556 are connected to each other via a bus 558.

The digital data supplied from the receiver section 56 is stored in the holographic memory 552. Thus the holographic memory 552 stores a holographic image of the received ultrasound.

The data processor 550 performs predetermined data processings on the respective data stored in the holographic memory 552, the data memory 554 and the image memory 556. Through the data processings, and based on the holographic image data stored in the holographic memory 552, three-dimensional (3D) positions of the ultrasound sources are calculated. The calculation is performed using a technique such as inverse propagation or inverse Fourier transformation. The calculated 3D positions of the ultrasound sources are stored in the data memory 554.

The data processor 550 also produces an image representing distribution of the ultrasound sources based on the 3D positional data stored in the data memory 554. The image is formed as a 3D image viewed from a desired viewpoint or as a tomographic image taken through a desired cross section. The image is stored in the image memory 556.

The image producing section 514 is connected with a display section 516. The display section 516 is supplied with image data from the image producing section 514 and displays an image based on the image data.

The receiver section 56, the image producing section 514, the display section 516 and the driving section 524 are connected to a control section 518. The control section 518 supplies control signals to these sections to control their operation. The ultrasonic imaging is executed under control of the control section 518.

The control section 518 is connected with an operating section 520. The operating section 520 is used by the operator to input desired commands and information to the control section 518. The operating section 520 is comprised of an operating panel including several operating devices such as a keyboard and the like.

The operation of the present apparatus will now be described. The operator positions the ultrasonic probe 52 and the electromagnetic wave irradiator 522 at desired positions on the subject 54, and operates the operating section 520 to start the imaging.

The imaging is then executed under control of the control section 518. The control section 518 controls the driving section 524 to drive the electromagnetic wave irradiator 522 to generate electromagnetic wave pulses like, for example, those shown in FIG. 2(*b*). The pulse-like warming by the electromagnetic wave pulses causes the individual microballoons in the microballoon contrast agent 540 to resonate as shown in FIG. 2(*c*), thereby generating ultrasound. The intensity of the generated ultrasound is appropriately regulated by varying the intensity of the warming, i.e., the intensity of the applied electromagnetic waves.

The ultrasound thus generated is sound generated by the microballoons per se, not echoes. Therefore, no 'main echo or its tailing' is involved because, unlike when echoes are generated, the imaging does not rely on return time to represent the distance to the microballoon. That is, the microballoons generate ultrasound signals having no tailing.

The ultrasound generated by the individual microballoons reach the 2D array 532 of the ultrasonic probe 52 as spherical waves, and their wavefronts propagate on the surface of the 2D array 532 describing concentric circles.

The ultrasound is received by the individual ultrasonic transducers 530 in the 2D array 532. The receiver section 56 produces a holographic image of the ultrasound based on the respective received signals of the ultrasonic transducers 530 in the 2D array 532.

The holographic image is stored in the holographic memory 552 in the image producing section 514. The data processor 550 uses the holographic image data stored in the holographic memory 552 to generate 3D distribution data of the ultrasound sources, i.e., 3D positional data of the individual microballoons, through an inverse propagation technique or an inverse Fourier transformation technique. Since there is no tailing in the received ultrasonic signals, the generated 3D distribution data of the microballoons contains no tailing. Such 3D distribution image data is stored in the data memory 554.

The data processor 550 produces a 3D image viewed from a certain viewpoint based on the 3D distribution image data, and stores the image in the image memory 556. The viewpoint is appropriately selected by the operator through the operating section 520.

Figure 6:
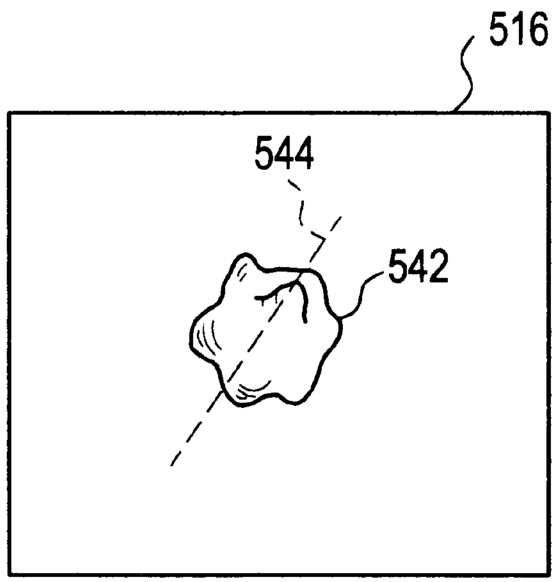
FIG. 6 is a schematic representation of an image displayed in the apparatus.

The image data stored in the image memory 556 is supplied into the display section 516 and displayed as a visible image. This gives a 3D contrast image 542 of the microballoon contrast agent 540 as exemplarily shown in FIG. 6. By varying the selected viewpoint, 3D contrast images viewed from various viewpoints can be displayed. The 3D contrast image 542 is a sharp one with no tailing.

Figure 7:
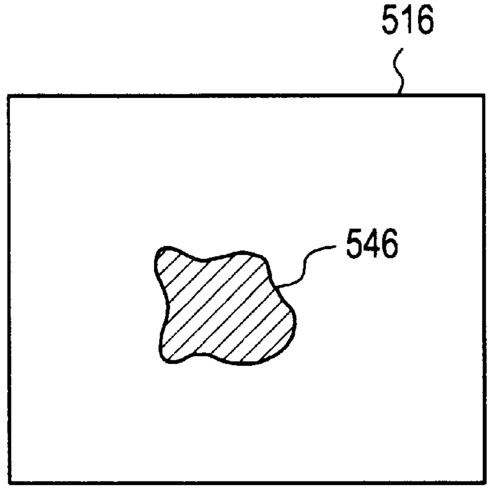
FIG. 7 is a schematic representation of another image displayed in the apparatus.

When the operator specifies a desired cross section using a line cursor 544 on the screen, the data processor 550 produces a contrast image taken through the specified cross section. This gives a cross-sectional contrast image 546 as exemplarily shown in FIG. 7. The cross-sectional contrast image 546 may be rendered either as a tomographic image or as an orthographic image according to the specification of the cross section. The cross-sectional contrast image 546 also is a sharp one with no tailing.

The ultrasonic probe 52 employed may comprise a one-dimensional (1D) array of the ultrasonic transducers. In this case, the present apparatus is an ultrasonic imaging apparatus for producing tomographic images.

Moreover, the ultrasound generated by the microballoons may be subjected to receive beamforming in the receiver section 56. The receive beamforming is carried out by a phased additive operation on the received signals from a plurality of ultrasonic transducers. A region to be imaged is scanned in a sound-ray sequential manner by changing the direction of the received beam in sequence to acquire the respective ultrasonic signals generated by the microballoons through which a sound ray passes. In this case, by extracting a desired signal range on the sound ray via a range gate, a desired internal region in the subject 54 can exclusively be imaged.

Figure 8:
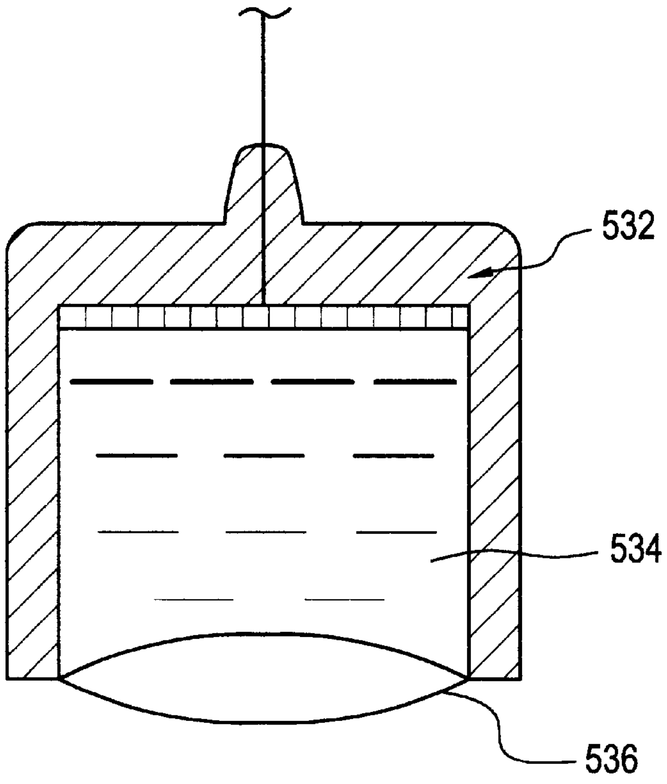
FIG. 8 is a schematic representation of an exemplary ultrasonic probe in the apparatus.

Furthermore, as exemplarily shown in FIG. 8, the ultrasonic probe 52 employed may be of a type which is provided with an acoustic lens 536 and an ultrasonic transmitting medium 534 such as water between the front surface of the 2D array 532 and the acoustic lens 536 so that an acoustic image is focused on the surface of the 2D array 532 by the acoustic lens 536. In this case, by using the received signals of the individual ultrasonic transducers as pixel values, an orthographic image of the contrast agent image can be obtained.

In addition, although electromagnetic wave warming is preferred because of its ease of implementation, the means for thermally exciting the microballoons is not limited to this type and warming means utilizing other energies such as an electric field, a magnetic field or light may be employed depending upon the properties of the subject 54.

Figure 9:
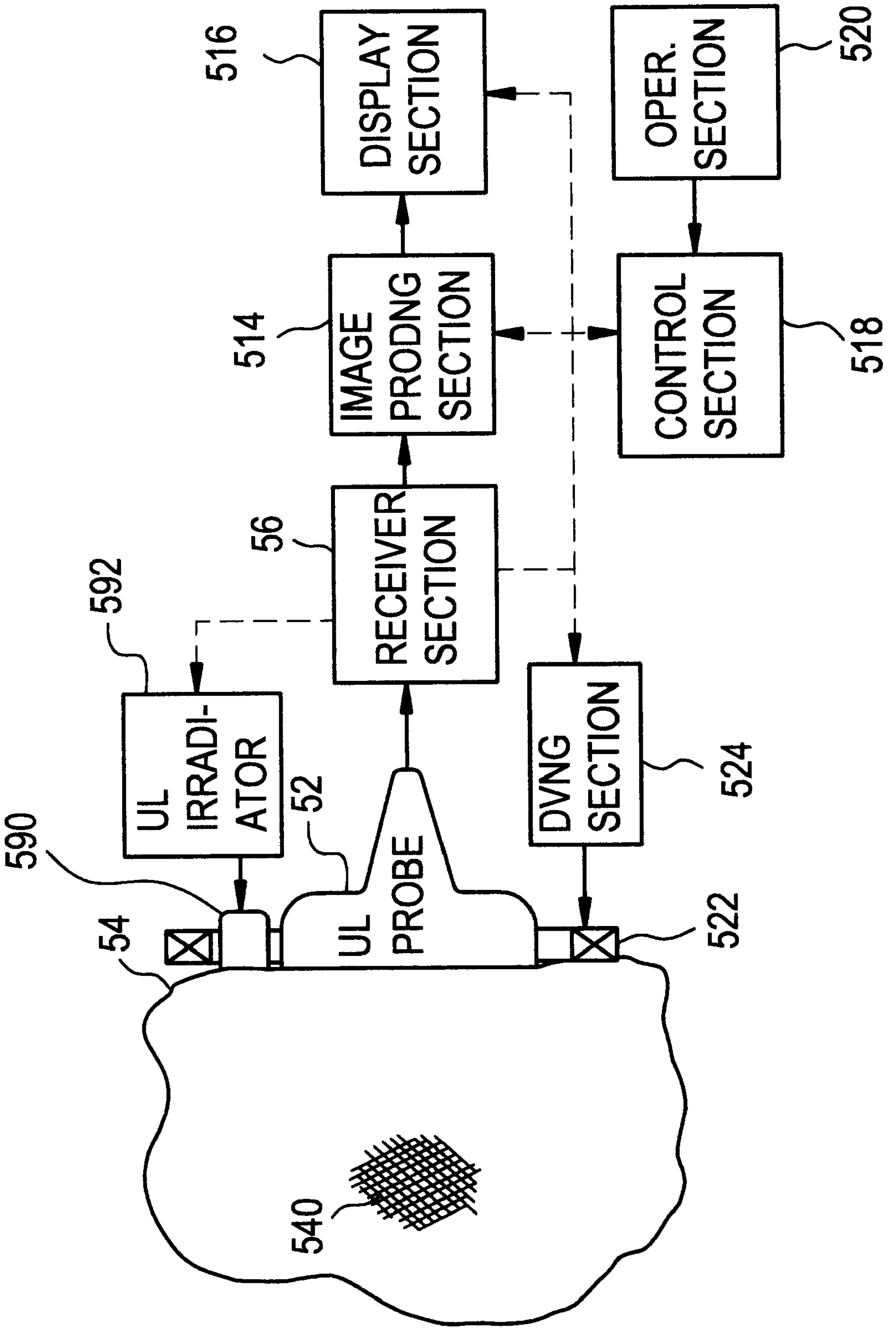
FIG. 9 is a block diagram of an apparatus in accordance with another embodiment of the present invention.

FIG. 9 shows another embodiment of the present invention. The configuration thereof represents an embodiment of the apparatus of the invention, and the operation thereof represents an embodiment of the method of the invention.

In FIG. 9, the same reference symbols denote the same components as those in FIG. 1 and explanation thereof will be omitted. In this embodiment, an ultrasound irradiator 590 abutting against the subject 54 emits ultrasound toward the interior of the subject 54. The ultrasound irradiator 590 is composed of, for example, ultrasonic transducers and is configured to be driven by a driving section 592 to emit nondirectional ultrasound having a predetermined frequency $f_0$.

The frequency $f_0$ is selected to differ from the resonance frequency $f_s$ of the microballoons. For example, if the resonance frequency $f_s$ of the microballoons is 1.8 MHz, then the frequency of the emitted ultrasound $f_0$ is selected as 1.5 MHz. Moreover, the intensity (level) of the ultrasound irradiation is selected within the range that does not break the microballoons and does not affect resonance.

The driving section 592 is controlled by the control section 518. Under this control, ultrasound is emitted, for example, synchronously with the ultrasound receive time period shown in FIG. 2(*d*). That is, ultrasound is emitted while the microballoons are resonating. The ultrasound may be continuously emitted while the present apparatus is activated. This is preferable for simplifying control. On the other hand, emitting the ultrasound synchronously with the receive time period is preferable for eliminating unnecessary irradiation time.

When the microballoons resonating at a frequency $f_s$ are subjected to ultrasound of a frequency $f_0$, the individual microballoons generate ultrasonic signals having a frequency of $f_r=f_0\pm f_s$ by the frequency translation effect on the microballoons.

The ultrasonic probe 52 receives such ultrasonic signals. The receiver section 56 extracts ultrasonic signals having a frequency of, for example, $f_r=f_0+f_s$ from the generated ultrasonic signals through a filter (not shown). The extracted ultrasonic signals have a frequency of, for example, 3.3 MHz. The image producing section 514 performs image production based on these signals in a similar manner as described above.

Obviously, the ultrasonic signals having a frequency $f_r$ do not involve a problem such as tailing because they are obtained simply by a frequency translation of the ultrasonic signals generated by resonance of the microballoons. Thus, an image produced based on these ultrasonic signals becomes a sharp one containing no tailing.

Besides, this embodiment has an additional advantage that the signal intensity of the received ultrasound can be properly adjusted by appropriately regulating the level of the emitted ultrasound within a range that does not affect resonance of the microballoons. Moreover, this embodiment is preferable because it enables the frequency of the received ultrasonic signals to be properly adjusted by selecting the frequency of the emitted ultrasound.

Also in this embodiment, the ultrasonic probe 52 may be of a type which comprises a 1D array of ultrasonic transducers, and the ultrasonic probe such as that shown in FIG. 8 may be employed. Also, the means for thermally exciting the microballoons may be of a type which employs an electric field, a magnetic field, light or the like as described above.

Although the preceding description has been made on examples in which distribution of the microballoons is visualized, it is obvious that dynamics of the microballoons may be visualized by conducting an appropriate number of repetitions of the thermal excitation of the microballoons and the subsequent ultrasound reception, applying a difference operation or higher-order filter operation on the obtained data before or after to producing an image, and performing, for example, a moving target indication (MTI) processing which extracts variation exclusively or a processing representing Doppler imaging.

Many widely different embodiments of the invention may be configured without departing from the spirit and the scope of the present invention. It should be understood that the present invention is not limited to the specific embodiments described in the specification, except as defined in the appended claims.

What is claimed is:

1. In an ultrasonic imaging method comprising the steps of:

- infusing a microballoon contrast agent into a subject;
- exciting the microballon contrast agent to cause the microballoon to produce ultrasound; and
- producing an image based on the ultrasound produced by the excited microballoons; the improvement wherein
- the microballoon contrast agent is excited thermally-to cause the microballoons to resonate and produce ultrasound.

2. The method of claim 1, wherein the thermal excitation is produced by signals selected from the group consisting of electromagnetic waves, electric field, magnetic field and light.

3. The method of claim 2, wherein the thermal excitation is produced by an electromagnetic wave of a frequency between 10–2,450 MHz.

4. The method of claim 3, wherein the electromagnetic waves are provided in a series of pulses.

5. In an ultrasonic imaging apparatus comprising:

- means for infusing a microballoon contrast agent into a subject;
- means for exciting said microballoon contrast agent to cause the microballoons to produce ultrasound; and
- means for producing an image based on the ultrasound produced by the excited microballoons; the improvement comprising:
- said means for exciting comprising means for thermally exciting said microballoon contrast agent to cause said microballons to resonate and produce ultrasound.

6. The apparatus of claim 5, wherein said means for thermally exciting comprises means for utilizing a signal selected from the group consisting of electromagnetic waves, electric field, magnetic field, and light.

7. The apparatus of claim 6, wherein the electromagnetic waves have a frequency of between 10 to 2,450 MHz.

8. The apparatus of claim 7, wherein the electromagnetic waves are in the form of pulses.

9. The apparatus of claim 5, wherein said means for producing an image comprises means for producing a three dimensional image from ultrasound generated in three dimensions.

10. The apparatus of claim 5, wherein said means for producing an image comprises means for producing an image in two dimensions from ultrasound generated in three dimensions.

* * * * *